(12) United States Patent
Abunassar

(10) Patent No.: US 9,782,280 B2
(45) Date of Patent: *Oct. 10, 2017

(54) OPTIMAL RATIO OF POLAR AND BENDING MOMENT OF INERTIA FOR STENT STRUT DESIGN

(71) Applicant: Abbott Cardiovascular Systems Inc., Santa Clara, CA (US)

(72) Inventor: Chad Abunassar, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/992,199

(22) Filed: Jan. 11, 2016

(65) Prior Publication Data
US 2016/0120669 A1 May 5, 2016

Related U.S. Application Data

(62) Division of application No. 13/707,342, filed on Dec. 6, 2012, now Pat. No. 9,241,814, which is a division of application No. 12/765,080, filed on Apr. 22, 2010, now Pat. No. 8,328,863.

(51) Int. Cl.
| A61F 2/82 | (2013.01) |
| A61F 2/89 | (2013.01) |
| A61F 2/958 | (2013.01) |
| A61F 2/915 | (2013.01) |
| A61F 2/848 | (2013.01) |

(52) U.S. Cl.
CPC .............. *A61F 2/89* (2013.01); *A61F 2/82* (2013.01); *A61F 2/915* (2013.01); *A61F 2/958* (2013.01); *A61F 2/848* (2013.01); *A61F 2002/825* (2013.01); *A61F 2002/91558* (2013.01); *A61F 2002/91566* (2013.01); *A61F 2230/0013* (2013.01); *A61F 2230/0026* (2013.01); *A61F 2250/0036* (2013.01); *A61F 2250/0039* (2013.01)

(58) Field of Classification Search
CPC .... A61F 2230/0026; A61F 2002/30158; A61F 2/24–2/2424
See application file for complete search history.

(56) References Cited

U.S. PATENT DOCUMENTS

| 5,807,404 A | 9/1998 | Richter |
| 5,928,280 A | 7/1999 | Hansen et al. |
| 5,968,088 A | 10/1999 | Hansen et al. |
| 6,001,123 A | 12/1999 | Lau |
| 6,017,362 A | 1/2000 | Lau |
| 6,183,506 B1 | 2/2001 | Penn et al. |
| 6,197,047 B1 | 3/2001 | Kranz |

(Continued)

*Primary Examiner* — Thomas J Sweet
*Assistant Examiner* — Rebecca Preston
(74) *Attorney, Agent, or Firm* — Fulwider Patton LLP

(57) ABSTRACT

An intravascular stent is provided to be implanted in coronary arteries and other body lumens. The transverse cross-section of at least some of the stent struts have a ratio of polar and bending moments of inertia, which results in optimal resistance to stent twisting. This resistance to twisting ratio for the stent struts minimizes out of plane twisting of the struts or projecting edges of the struts when the stent is expanded from a compressed diameter to an expanded diameter in a coronary artery.

7 Claims, 2 Drawing Sheets

(56) References Cited

U.S. PATENT DOCUMENTS

| | | |
|---|---|---|
| 6,217,608 B1 | 4/2001 | Penn et al. |
| 6,231,598 B1 | 5/2001 | Berry et al. |
| 6,241,762 B1 | 6/2001 | Shanley |
| 6,245,101 B1 | 6/2001 | Drasler et al. |
| 6,273,911 B1 | 8/2001 | Cox et al. |
| 6,287,335 B1 | 9/2001 | Drasler et al. |
| 6,287,336 B1 | 9/2001 | Globerman et al. |
| 6,293,967 B1 | 9/2001 | Shanley |
| 6,312,460 B2 | 11/2001 | Drasler et al. |
| 6,375,677 B1 | 4/2002 | Penn et al. |
| 6,419,693 B1 | 7/2002 | Fariabi |
| 6,451,051 B2 | 9/2002 | Drasler et al. |
| 6,464,720 B2 | 10/2002 | Boatman et al. |
| 6,468,302 B2 | 10/2002 | Cox et al. |
| 6,475,237 B2 | 11/2002 | Drasler et al. |
| 6,482,166 B1 | 11/2002 | Fariabi |
| 6,511,505 B2 | 1/2003 | Cox et al. |
| 6,527,799 B2 | 3/2003 | Shanley |
| 6,562,065 B1 | 5/2003 | Shanley |
| 6,602,284 B2 | 8/2003 | Cox et al. |
| 6,676,697 B1 | 1/2004 | Richter |
| 6,736,843 B1 | 5/2004 | Fariabi |
| 6,758,860 B1 | 7/2004 | Penn et al. |
| 6,796,997 B1 | 9/2004 | Penn et al. |
| 6,827,734 B2 | 12/2004 | Fariabi |
| 6,852,124 B2 | 2/2005 | Cox |
| 6,858,037 B2 | 2/2005 | Penn |
| 6,878,162 B2 | 4/2005 | Bales et al. |
| 6,881,223 B2 | 4/2005 | Penn et al. |
| 6,887,264 B2 | 5/2005 | Penn et al. |
| 7,044,963 B1 | 5/2006 | Richter |
| 7,094,255 B2 | 8/2006 | Penn et al. |
| 7,160,321 B2 | 1/2007 | Shanley |
| 7,172,623 B2 | 2/2007 | Hansen et al. |
| 7,179,288 B2 | 2/2007 | Shanley |
| 7,258,697 B1 | 8/2007 | Cox et al. |
| 7,279,004 B2 | 10/2007 | Shanley |
| 7,294,146 B2 | 11/2007 | Chew et al. |
| 7,326,244 B2 | 2/2008 | Drasler et al. |
| 7,534,257 B2 | 5/2009 | Richter |
| 7,601,382 B2 | 10/2009 | Weber et al. |
| 7,709,045 B2 | 5/2010 | Flanagan |
| 7,875,069 B2 | 1/2011 | Heaney et al. |
| 8,070,794 B2 | 12/2011 | Issenmann |
| 8,551,156 B2 | 10/2013 | Wack et al. |
| 9,241,814 B2 * | 1/2016 | Abunassar .............. A61F 2/915 |
| 2003/0187498 A1 | 10/2003 | Bishop |
| 2004/0098090 A1 | 5/2004 | Williams et al. |
| 2009/0187215 A1 | 7/2009 | Mackiewicz et al. |
| 2011/0295356 A1 * | 12/2011 | Abunassar .............. A61F 2/915 623/1.15 |

* cited by examiner

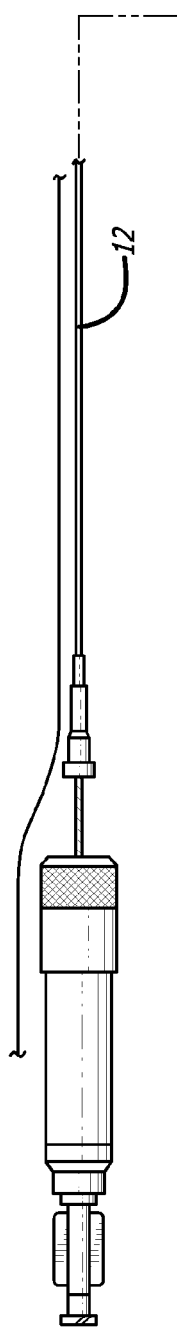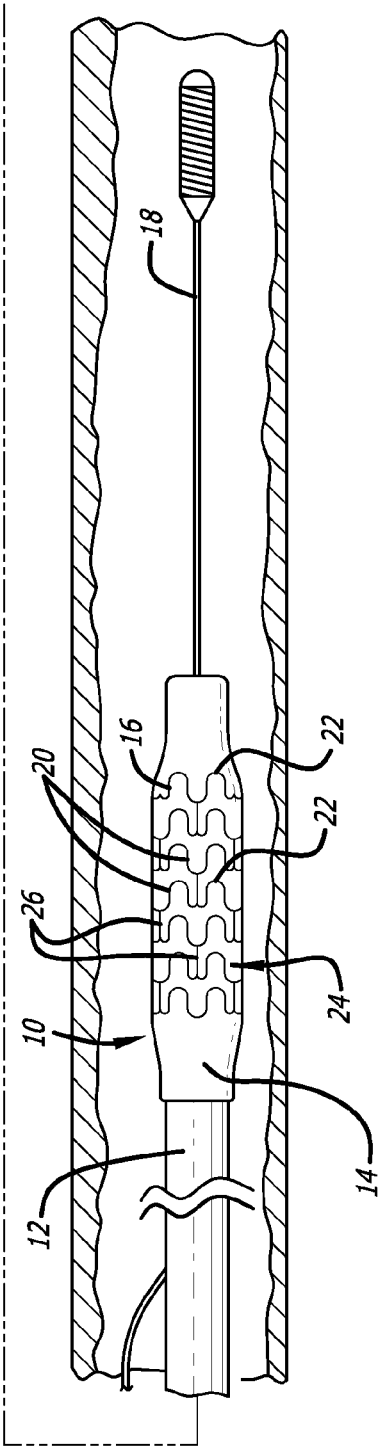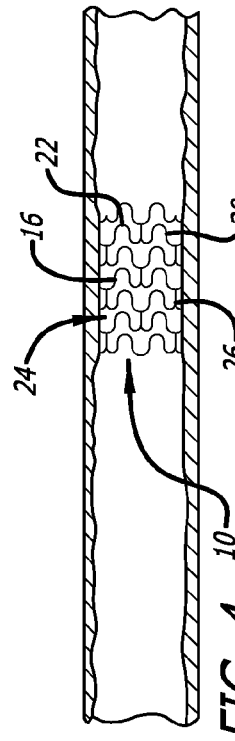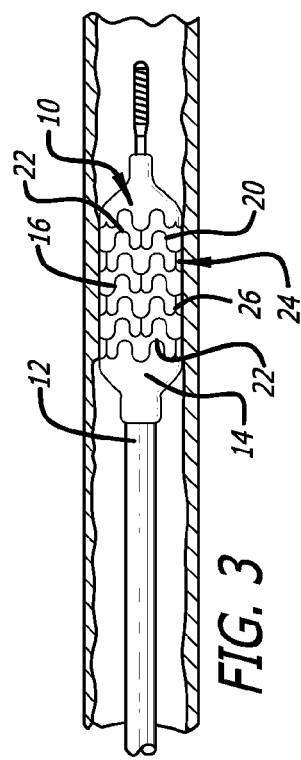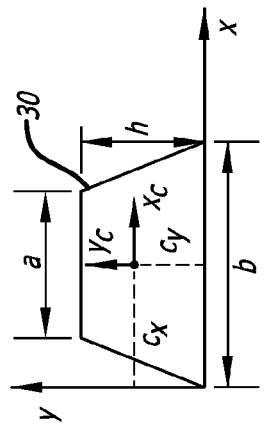
FIG. 2
FIG. 3
FIG. 4
FIG. 5

OPTIMAL RATIO OF POLAR AND BENDING MOMENT OF INERTIA FOR STENT STRUT DESIGN

CROSS-REFERENCE TO RELATED APPLICATIONS

This application is a division of U.S. Ser. No. 13/707,342, filed Dec. 6, 2012, which issued as U.S. Pat. No. 9,241,814 on Jan. 26, 2016, which is a division of U.S. Ser. No. 12/765,080, filed Apr. 22, 2010, which issued as U.S. Pat. No. 8,328,863 on Dec. 11, 2012, the contents of which are hereby incorporated by reference.

BACKGROUND

The invention relates to expandable stents which are adapted to be implanted into a patient's body lumen such as a coronary artery, in order to maintain the patency thereof. Stents are useful in the treatment of atherosclerotic stenosis in the coronary arteries, and other vessels in the body.

Stents are generally tubular-shaped devices which function to hold open a segment of a blood vessel or coronary artery, or other anatomical lumen. They also are useful to support and hold back a dissected arterial lining which can occlude the fluid passageway therethrough. The delivery and deployment of stents in the coronary arteries are well known in the art and various types of catheters are used, along with guide wires, to position and implant a stent in an artery.

Stents typically are formed from thin-walled metal tubing that is laser cut to form a pattern of stent struts in the tubing wall. The stent struts will typically have a generally rectangular cross-section when formed by the laser cutting. One of the difficulties encountered in forming stents having struts with a rectangular cross-section is that the ability to uniformly compress the stent onto the balloon portion of a catheter and expand the stent for implanting into a coronary vessel is not uniform and results in twisting or projecting edges. For example, in U.S. Pat. No. 5,514,154, which is incorporated herein by reference, the struts have an aspect ratio resulting in projecting edges and twisting when the stent is expanded and implanted in a coronary artery.

What has been needed and heretofore unavailable is a strut aspect ratio that provides a stent that can be uniformly compressed and expanded without developing out-of-plane twisting of the stent struts or projecting edges of the struts.

SUMMARY OF THE INVENTION

The present invention is directed to a stent formed from an elongated tubular member having struts that form a stent pattern. The struts have a transverse cross-section that is generally trapezoidal, while the edges may be electro-polished so that the edges are rounded while still maintaining the generally trapezoidal cross-sectional shape. The struts have a torsional resistance ratio of about 1.51, which is the optimum ratio of torsional resistance to bending resistance in order to compress the stent onto the balloon portion of a catheter and expand the stent into an artery without the struts twisting out-of-plane or forming projecting edges.

Other features and advantages of the present invention will become more apparent from the following detailed description of the invention when taken in conjunction with the accompanying exemplary drawings.

BRIEF DESCRIPTION OF THE DRAWINGS

FIG. 2 is an elevational view depicting a stent uniformly compressed onto a balloon portion of a catheter and having a torsional resistance to twisting of about 1.51.

FIG. 3 is an elevational view depicting an expanded stent on a balloon and having torsional resistance to twisting that minimizes out-of-plane twisting of the struts and minimizes projecting edges.

FIG. 4 is an elevational view depicting an expanded stent having struts having a height and width that minimizes out-of-plane twisting of the struts and minimizes projecting edges.

FIG. 5 is a transverse cross-sectional view of a strut of the stent of the present invention having a substantially trapezoidal shape.

DETAILED DESCRIPTION OF THE PREFERRED EMBODIMENTS

Figure 1:
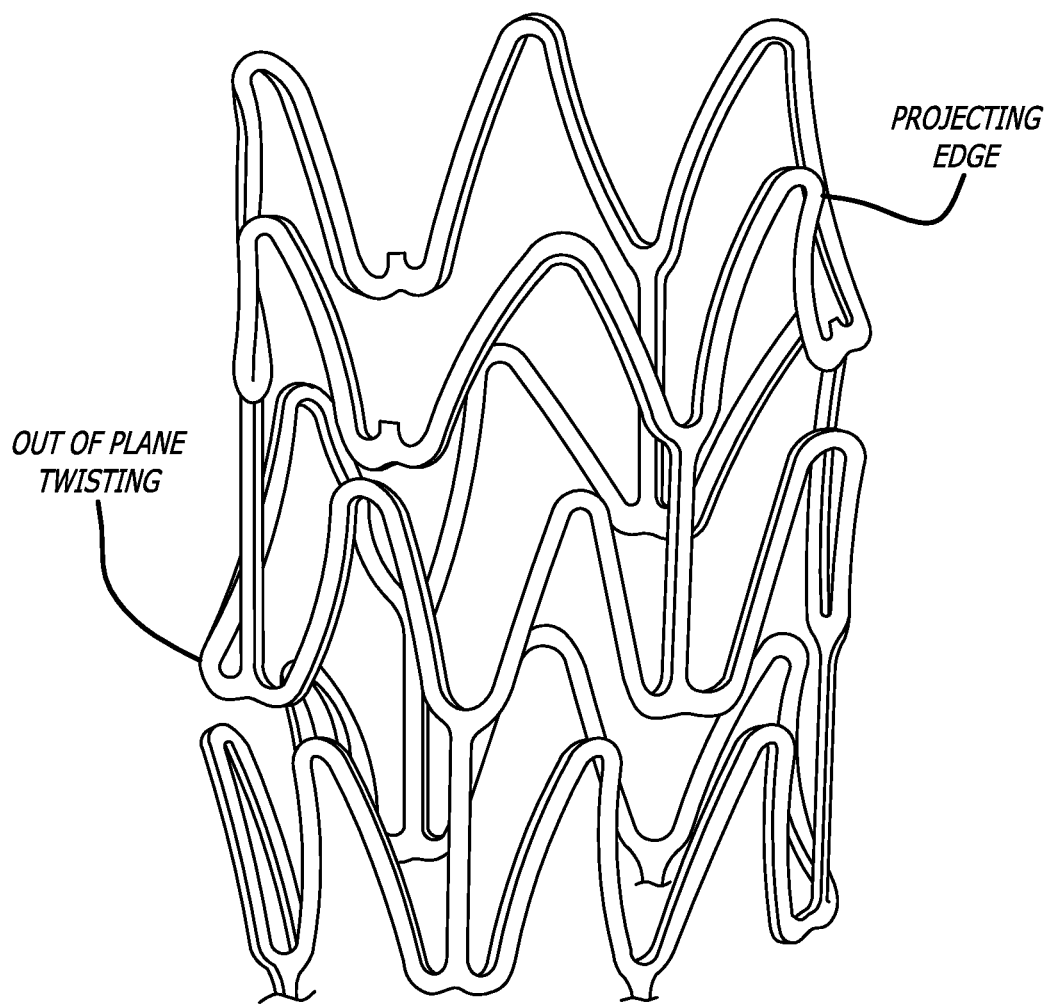
FIG. 1 is an enlarged, partial perspective view of a prior art stent showing a portion of a strut segment projecting radially outwardly and twisting out of plane after expansion.

Intravascular stents are generally formed by laser cutting a pattern in a thin walled tube and then etching or electropolishing the laser cut stent. This typically produces a stent strut that has a transverse cross-section that is generally square or rectangular with somewhat rounded corners. First generation stent strut cross-sections were generally square in nature, however, clinical trials have shown that thinner struts (less radial thickness) perform better with respect to limiting the formation of restenosis. This conclusion is attributed to the observation that radially thinner stent struts drive a reduction in arterial injury and thus provide less destruction of local hemodynamics when compared to radially thicker stent struts. Even though thin stent struts provide these clinical benefits, they also must be made stronger and/or stiffer to provided sufficient radial strength and stiffness in order to properly scaffold a target lesion or arterial wall. These thin struts therefore exhibit higher aspect ratios (strut width÷strut height) greater than one-to-one (square) to provide sufficient bending stiffness to prevent the stent struts from closing due to strut bending loads. In designing a strut with a high aspect ratio, however, the typical strut torsional resistance is relatively low compared to a square (symmetric) cross-section. When torsional resistance to twisting is low compared to the bending resistance of a stent strut (which is the case for high aspect ratio struts), the stent strut may twist slightly out of plane when undergoing initial elastic deformation. As shown by the prior art stent in FIG. 1, this effect is more severe under large plastic deformation due to compressing or crimping the stent onto the balloon portion of a catheter or during stent expansion into an artery. This localized twisting leads to irregular out-of-plane strut deformations, which are associated with local strut fracture, increased local arterial injury, poor local scaffolding and subsequent plaque prolapse, poor drug delivery (for stents having a drug coating), and an incomplete strut apposition with a potential for associated thrombosis.

As stent technologies advance, an overriding interest of stent designers is the ability of a stent strut to overcome stress and fatigue failures. This ability is directly related to the strain and stress distribution throughout the stent structure. A stent is typically made from a number of stent rings that create a scaffold structure, and each of these stent rings include stent struts. These stent struts are commonly rectangular although they may also have round, oval, or square geometries. Nonetheless, in the sense of rectangular strut dimensions the strut is usually denoted as having a strut width and a strut thickness (radial thickness). Since stent structures are expanded within body vessels and are generally placed under pulsatile loading during their use, the stresses that are seen throughout the stent include compressive and tensile stresses. The distribution of these stresses throughout the strut determines how evenly the scaffold will expand. For example, the stent rings usually have what are referred to as stent crowns and these are the undulating portions (curved struts) that connect one stent strut to an adjacent stent strut. As the stent is expanded these stent crowns tend to open and compressive stresses are placed toward the outer edge of the crown while tensile stresses are placed toward the inner edge of the crown. The stresses are then distributed along the stent strut going from a high stress portion near the stent crown to a portion that essentially has no stress toward the center of the strut. Due to the stress distributions it is not uncommon for there to be a torque applied to the strut, which can cause the strut and the crown to twist out of plane. This behavior is particularly common in thinner struts because the strut has less resistance to the applied torque and therefore twists more easily. Since the industry is moving toward thinner struts given that the stent design provides improvements to physiological response and device deliverability, it is anticipated that strut twist will continue to be an issue and therefore there is a need for a solution that will prevent strut twisting.

In keeping with the present invention, a stent strut cross-section is provided to ensure optimal stent crimping and stent expansion. More specifically, the present invention design provides uniform stent expansion that provides the following potential benefits: maximized radial strength with minimal strut thickness; uniform strut apposition; reliable side-branch access; reduced local vessel injury; improved uniformity of drug delivery; and improved circular expansion. Further, the strut cross-section of the present invention is associated with an improved crimp profile, uniformity in crimping, and improved stent retention on the balloon portion of a catheter.

In keeping with the invention, and referring to FIGS. 2-4, a stent delivery assembly 10 includes a rapid exchange catheter 12 which has an expandable balloon 14 at its distal end. An intravascular stent 16 is mounted on the balloon and compressed firmly onto the balloon in a known manner. A guide wire 18 extends through at least a portion of the distal end of catheter 12 so that the catheter can slide along the guide wire and into the coronary arteries, also in a known manner. Once the catheter 12 positions the stent in a coronary artery, the stent can be expanded as shown in FIGS. 3 and 4 so that the stent is pressed into the coronary artery or it is permanently implanted to hold open the artery and prevent recoil.

In one embodiment of the present invention, as shown in FIGS. 3 and 4, stent 16 has multiple linear stent struts 20 (sometimes referred to as bar arms) interconnecting with curved stent struts or crowns 22. A stent pattern having linear stent struts and crown struts is generally formed from a tubular member by laser cutting in a known manner which is well known in the art. The stent struts form cylindrical rings 24 that extend circumferentially and can be compressed radially inwardly onto the balloon 14, or expanded radially outwardly when the balloon is expanded in order to implant the stent in a coronary artery. The rings are interconnected with links 26 and the linear stent struts 20 and curved stent struts 22 will open and close as the rings are expanded or compressed.

In one aspect of the invention, as shown in FIG. 5, one or more of the linear stent struts 20 and one or more of the crown struts 22 have a transverse cross-section that is substantially a polygon 30. The struts have a width "a" and a width "b" and a height "h" providing polygon 30 that will resist strut twisting. The thickness is shown as "h" and is approximately the same across the full width of the strut. However, the width is represented by two separate dimensions "a" and "b". In this figure, "a" is intended to be the width of the strut along the inner surface of the stent while "b" is the strut width along the outer surface of the stent. In FIG. 5, polygon 30 is trapezoidal-shaped.

The moments of inertia for a trapezoidal-shaped polygonal strut can be calculated in the manner shown in Table 1. The following definitions of the various moments of inertia are provided. "$I_{xc}$" represents the bending moment of inertia about the x-axis (see FIG. 5) and is the resistance of the strut to bend out-of-plane, or in the radial direction of a circularly deployed stent. "$I_{yc}$" represents the bending moment of inertia about the y-axis (FIG. 5), and is the resistance of the strut to bend in plane in the tangential direction. A high "$I_{yc}$" value is desired in the design of a stent that resists collapse under radial pressure from the arterial wall. When a stent is subjected to radial loading from the artery, the stent structure deforms tangentially to accommodate a global mode of radial compression (i.e., all of the crowns close slightly by bending closer together). "J" represents the torsional (twisting) resistance of a stent strut. While it is desired to use a strut that maximizes "$I_{yc}$" to produce a stent that is the most radially stiff/strong, if the strut is too wide, "$I_{yc}$" is relatively high and "J" relatively low. Relatively slender strut cross-sections (high aspect ratio) twist very easily, while square strut cross-sections provide the most resistance to twist.

Equations exist for calculating the moment of inertia $I_{xc}$ about the x-axis, the moment of the inertia $I_{yc}$ about the y-axis, and the polar moment of the inertia $I_{zc}$ about the z-axis (extending out f the page in FIG. 5). The moment of inertia "$I_{xc}$" about the x-axis is calculated as follows.

$$I_{xc} = \frac{h^3(a^2 + 4ab + b^2)}{36(a+b)}$$

The moment of inertia "$I_{yc}$" about the y-axis is calculated as follows.

$$I_{yc} = \frac{h(a+b)(a^2+b^2)}{48}$$

The polar moment of inertia "$J_{zc}$" about the z-axis is calculated as follows.

$$J_{zc} = \frac{h(16h^2ab + 4h^2b^2 + 4h^2a^2 + 3a^4 + 6a^2b^2 + 6a^3b + 6ab^3 + 3b^4)}{144(a+b)}$$

Referring to Table 1 (in inches), these calculations can be made for various dimensions in the range of typical stent dimensions. For example, a range of strut width "a" from 0.0010-inch to 0.0056-inch can be analyzed along with a strut width "b" range from 0.0032-inch to 0.0060-inch. Additionally, a strut thickness "h" between 0.0022-inch and 0.0045-inch was analyzed for the purposes of the invention. It will be appreciated that other ranges may be analyzed in accordance with this invention, but these ranges are anticipated to be useful as at least one relevant stent embodiment for coronary artery use.

TABLE 1

| a | b | ab_average | h | Aspect Ratio | $J/I_{yc}$ |
|---|---|---|---|---|---|
| 0.0016 | 0.0032 | 0.0024 | 0.0032 | 0.75 | 2.540741 |
| 0.0018 | 0.0032 | 0.0025 | 0.0032 | 0.78125 | 2.479584 |
| 0.002 | 0.0032 | 0.0026 | 0.0032 | 0.8125 | 2.412672 |
| 0.0022 | 0.0032 | 0.0027 | 0.0032 | 0.84375 | 2.342566 |
| 0.0024 | 0.0032 | 0.0028 | 0.0032 | 0.875 | 2.271293 |
| 0.0026 | 0.0032 | 0.0029 | 0.0032 | 0.90625 | 2.200408 |
| 0.0028 | 0.0032 | 0.003 | 0.0032 | 0.9375 | 2.131065 |
| 0.003 | 0.0032 | 0.0031 | 0.0032 | 0.98675 | 2.06408 |
| 0.0032 | 0.0032 | 0.0032 | 0.0032 | 1 | 2 |
| 0.0034 | 0.0034 | 0.0034 | 0.0032 | 1.0625 | 1.885813 |
| 0.0036 | 0.0036 | 0.0036 | 0.0032 | 1.125 | 1.790123 |
| 0.0038 | 0.0038 | 0.0038 | 0.0032 | 1.1875 | 1.709141 |
| 0.004 | 0.004 | 0.004 | 0.0032 | 1.25 | 1.64 |
| 0.0042 | 0.0042 | 0.0042 | 0.0032 | 1.3125 | 1.580499 |
| 0.0044 | 0.0044 | 0.0044 | 0.0032 | 1.375 | 1.528926 |
| 0.0045 | 0.0045 | 0.0045 | 0.0032 | 1.40625 | 1.505679 |
| 0.002 | 0.006 | 0.004 | 0.0032 | 1.25 | 1.469333 |
| 0.005 | 0.0032 | 0.0041 | 0.0032 | 1.28125 | 1.571823 |
| 0.0052 | 0.0032 | 0.0042 | 0.0032 | 1.3125 | 1.538975 |
| 0.0054 | 0.0032 | 0.0043 | 0.0032 | 1.34375 | 1.508458 |
| 0.0056 | 0.0032 | 0.0044 | 0.0032 | 1.375 | 1.480102 |
| 0.002 | 0.0034 | 0.0027 | 0.0022 | 1.227273 | 1.60817 |
| 0.001 | 0.0034 | 0.0022 | 0.0022 | 1 | 1.694268 |
| 0.0012 | 0.0034 | 0.0023 | 0.0022 | 1.045455 | 1.687843 |
| 0.0014 | 0.0034 | 0.0024 | 0.0022 | 1.090909 | 1.674543 |
| 0.0016 | 0.0034 | 0.0025 | 0.0022 | 1.136364 | 1.655937 |
| 0.0018 | 0.0034 | 0.0026 | 0.0022 | 1.181818 | 1.633413 |
| 0.002 | 0.0034 | 0.0027 | 0.0022 | 1.227273 | 1.60817 |
| 0.0022 | 0.0034 | 0.0028 | 0.0022 | 1.272727 | 1.58121 |

Using the dimensional ranges described above, an average width "ab average" can be calculated from various strut widths "a" and "b" measured at the outer and inner edges of a trapezoidal stent strut, respectively. For a square stent strut cross-section, "a" is equal to "b" and also is equal to "ab average." This "ab average" width can be divided by the thickness "h" to find an aspect ratio.

This aspect ratio can be correlated empirically to the optimal strut configuration that will resist strut twisting. For example, in this example, it may be found that the ideal aspect ratio to resist strut twisting is the target value of 1.41 to 1.0. This determination may be made from building various stents with differing aspect ratios and then observing their behavior during expansion to find the strut configuration that performs best with respect to strut twist resistance and its combination with other relevant stent characteristics. Once the optimal aspect ratio is determined, the ratios of the various moments of inertia can be found by analyzing the ratio of $I_{xc}/I_{yc}$, $J/I_{xc}$, and $J/I_{yc}$ for the given strut cross section.

These ratios of moment of inertia may be used as guidelines for optimal strut configuration. For example, the ratio of $J/I_{yc}$ is a representative resistance to twisting compared to resistance to bending, for a given body. Practically speaking, when a strut is optimally configured, it will be able to bend and to resist twisting so that good scaffolding of the vessel is achieved. Therefore, the optimal aspect ratio described above is also the design to which the $J/I_{yc}$ is optimal. Therefore, the optimal $J/I_{yc}$ in this case is 1.51 (referencing Table 1).

Having found the optimal $J/I_{yc}$ ratio, any number of strut dimensional changes may be made by adjusting the strut width and thickness dimensions. In all cases, when the dimensions are modified, if they are changed to maintain a $J/I_{yc}$ ratio of 1.51, it is anticipated that resistance to twisting for the revised strut dimensions will be similarly optimized. For example, if the thickness is decreased, it will be possible to maintain the $J/Iy_c$ ratio by adjusting the dimensions "a" and "b" until the desired ratio is achieved. The modified strut section should have similar resistance to twisting as the original strut design, in that case.

While the invention has been illustrated and described herein in terms of its use as an intravascular stent, it will be apparent to those skilled in the art that the stent can be used in other instances such as to expand body lumens and other vessels in addition to coronary arteries. Other modifications and improvements can be made without departing from the scope of the invention.

What is claimed:

1. A stent, comprising:
   an elongated tubular member having struts forming a stent pattern comprising cylindrical rings connected by links;
   the struts having a transverse cross-section that is a four sided polygon, a first side and a second side are opposite each other and spaced apart by a distance h;
   a third side and a fourth side are opposite each;
   the first side and second side are parallel to each other and the third side and the fourth side are non-parallel to each other; and
   the lengths of the first side, second side, third side and fourth side are selected so that a ratio of twisting resistance (J) to bending resistance ($I_{yc}$) in the struts is in the range from 1.508458 to 1.538975.

2. The stent of claim 1, wherein the first side forms an inner surface of the elongated tubular member.

3. The stent of claim 2, wherein the second side forms an outer surface of the elongated tubular member.

4. The stent of claim 1, wherein the third side and the fourth side are longer than the second side.

5. The stent of claim 1, wherein the length of the first side is in the range from 0.0054 inch to 0.0052 inch and the second side is 0.0032 inch.

6. The stent of claim 5, wherein an aspect ratio of 1.34375 results from the first side length being 0.0054 inch, the second side length being 0.0032 inch, and the distance h being 0.0032 inch.

7. The stent of claim 5, wherein an aspect ratio 1.3125 results from the first side length being 0.0052 inch and the second side length being 0.0032 inch, and the distance h being 0.0032 inch.

* * * * *

UNITED STATES PATENT AND TRADEMARK OFFICE
CERTIFICATE OF CORRECTION

PATENT NO. : 9,782,280 B2  
APPLICATION NO. : 14/992199  
DATED : October 10, 2017  
INVENTOR(S) : Chad Abunassar Page 1 of 1

It is certified that error appears in the above-identified patent and that said Letters Patent is hereby corrected as shown below:

In the Claims

Column 6, Line 32, Claim 1, after "each" add "other"

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*